US010092438B2

(12) United States Patent
Salsbery

(10) Patent No.: US 10,092,438 B2
(45) Date of Patent: Oct. 9, 2018

(54) ADJUSTABLE LEG BRACE SYSTEMS AND METHODS

(71) Applicant: Dana Salsbery, Tidewater, OR (US)

(72) Inventor: Dana Salsbery, Tidewater, OR (US)

( * ) Notice: Subject to any disclaimer, the term of this patent is extended or adjusted under 35 U.S.C. 154(b) by 522 days.

(21) Appl. No.: 14/716,730

(22) Filed: May 19, 2015

(65) Prior Publication Data

US 2015/0335456 A1 Nov. 26, 2015

Related U.S. Application Data

(60) Provisional application No. 61/997,133, filed on May 23, 2014.

(51) Int. Cl.
*A61F 5/01* (2006.01)

(52) U.S. Cl.
CPC ............ *A61F 5/012* (2013.01); *A61F 5/0106* (2013.01)

(58) Field of Classification Search
CPC .......... A61F 5/0106; A61F 5/028; A61F 5/34; A61F 5/05816; A61F 5/012; A61H 9/0078; A61B 17/12; A61B 17/1325; A61B 17/135; A61B 17/132; A61B 17/1322
USPC ............................................... 602/13, 16, 26
See application file for complete search history.

(56) References Cited

U.S. PATENT DOCUMENTS

| 4,041,940 | A | * | 8/1977 | Frankel | A61F 5/0585 2/24 |
|---|---|---|---|---|---|
| 4,872,448 | A | * | 10/1989 | Johnson, Jr. | A41D 13/0568 128/DIG. 20 |
| 5,387,185 | A | * | 2/1995 | Johnson, Jr. | A61F 5/0585 128/882 |
| 5,588,956 | A | * | 12/1996 | Billotti | A61F 5/012 128/DIG. 20 |
| 7,011,641 | B1 | * | 3/2006 | DeToro | A61F 5/0125 602/16 |
| 2008/0086070 | A1 | * | 4/2008 | Meehan | A61F 5/0104 602/26 |
| 2014/0316317 | A1 | * | 10/2014 | Nace | A61F 5/0125 602/13 |
| 2014/0330184 | A1 | * | 11/2014 | Kilbey | A61F 5/0123 602/13 |

* cited by examiner

*Primary Examiner* — Ophelia A Hawthorne
(74) *Attorney, Agent, or Firm* — Mohr Intellectual Property Law Solutions, P.C.

(57) ABSTRACT

Leg braces configured to assist in straightening of a user's leg are shown and described. Each of the leg braces includes an anterior brace configured to be braced against an anterior portion of the leg proximal to the knee joint, having a selectively expandable and contractible bladder and an anterior brace attachment mechanism for attaching the anterior brace to a posterior brace. In some examples, each of the leg braces further includes the posterior brace configured to be braced against a posterior portion of the leg, the posterior brace having a rigid elongate base, an upper posterior brace attachment mechanism, and a lower posterior brace attachment mechanism for attaching the posterior brace to the leg below the knee joint.

20 Claims, 11 Drawing Sheets

ADJUSTABLE LEG BRACE SYSTEMS AND METHODS

CROSS REFERENCE TO RELATED APPLICATIONS

This application claims priority to U.S. Provisional Patent Application, Ser. No. 61/997,133, filed on May 23, 2014, which is hereby incorporated by reference for all purposes.

BACKGROUND

The present disclosure relates generally to adjustable leg brace systems and methods for straightening of a patient's leg. In particular, leg braces having an expandable and contractible bladder braced against a front portion of the patient's leg are described.

Often, after surgery and/or injury to a knee, a condition of "stiffness" can occur. Stiffness prevents movability of the leg around the knee between an extended position and a flexed position, which is required for carrying out many normal activities (e.g., walking, stair climbing, moving between standing and sitting, etc.). In many cases of stiffness, the leg is at least partially immobilized in a flexed and/or bent position around the stiff knee joint.

Known leg straightening methods and mechanisms are not entirely satisfactory for the range of applications in which they are employed. For example, existing methods generally include long term physical therapy. Long term physical therapy can be painful and costly for the patient. Further, the work of moving the leg towards a straight position can only occur during a limited period of time (i.e., while the patient is at the physical therapy appointment), and therefore, recovery is slow.

Another conventional leg straightening method includes a patient lying face down on a bed and allowing gravity to straighten the leg. Additionally, weights can be added to the patient's ankle to assist in straightening. This method, however, has the limitation that is awkward for the user and requires them to lie face down in bed for lengthy periods of time. Further, if weights are used in the gravity methods, it is difficult and/or awkward for the user to adjust the weights.

Thus, there exists a need for leg straightening methods and devices that improve upon and advance the design of known leg straightening methods. Examples of new and useful adjustable leg brace systems and methods for straightening of a patient's leg relevant to the needs existing in the field are discussed below.

SUMMARY

The present disclosure is directed to adjustable leg braces each configured to assist in straightening of the leg of a user around the user's knee joint. Each of the leg braces includes an anterior brace configured to be braced against an anterior portion of the leg proximal to the knee joint, the anterior brace having a bladder that is selectively expandable and selectively contractible and an anterior brace attachment mechanism for attaching the anterior brace to the posterior brace. In some examples, each of the leg braces further includes a posterior brace configured to be braced against a posterior portion of the leg, the posterior brace having a rigid elongate base, an upper posterior brace attachment mechanism for attaching the posterior brace to a region of the leg above the knee joint, and a lower posterior brace attachment mechanism for attaching the posterior brace to a region of the leg below the knee joint.

DETAILED DESCRIPTION

The disclosed adjustable leg braces will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, examples of various adjustable leg braces are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

With reference to FIGS. 1-11 a first example of an adjustable leg brace for straightening of a patient's leg, leg brace 100, will now be described. Leg brace 100 functions to provide a patient adjustable mechanism for straightening the patient's leg. Additionally or alternatively, leg brace 100 can be used to allow mobility of the user during the leg straightening process.

Leg brace 100 addresses many of the shortcomings existing with conventional methods for straightening a patient's leg during recovery from knee injury and/or surgery. For example, use of the leg brace is less costly than long term physical therapy. In another example, the patient can wear/use the leg brace as often as they like, thereby speeding the recovery process. Further, the leg brace is easily adjusted and manipulated by the user so that a pressure can be easily adjusted during wear.

Figure 1:
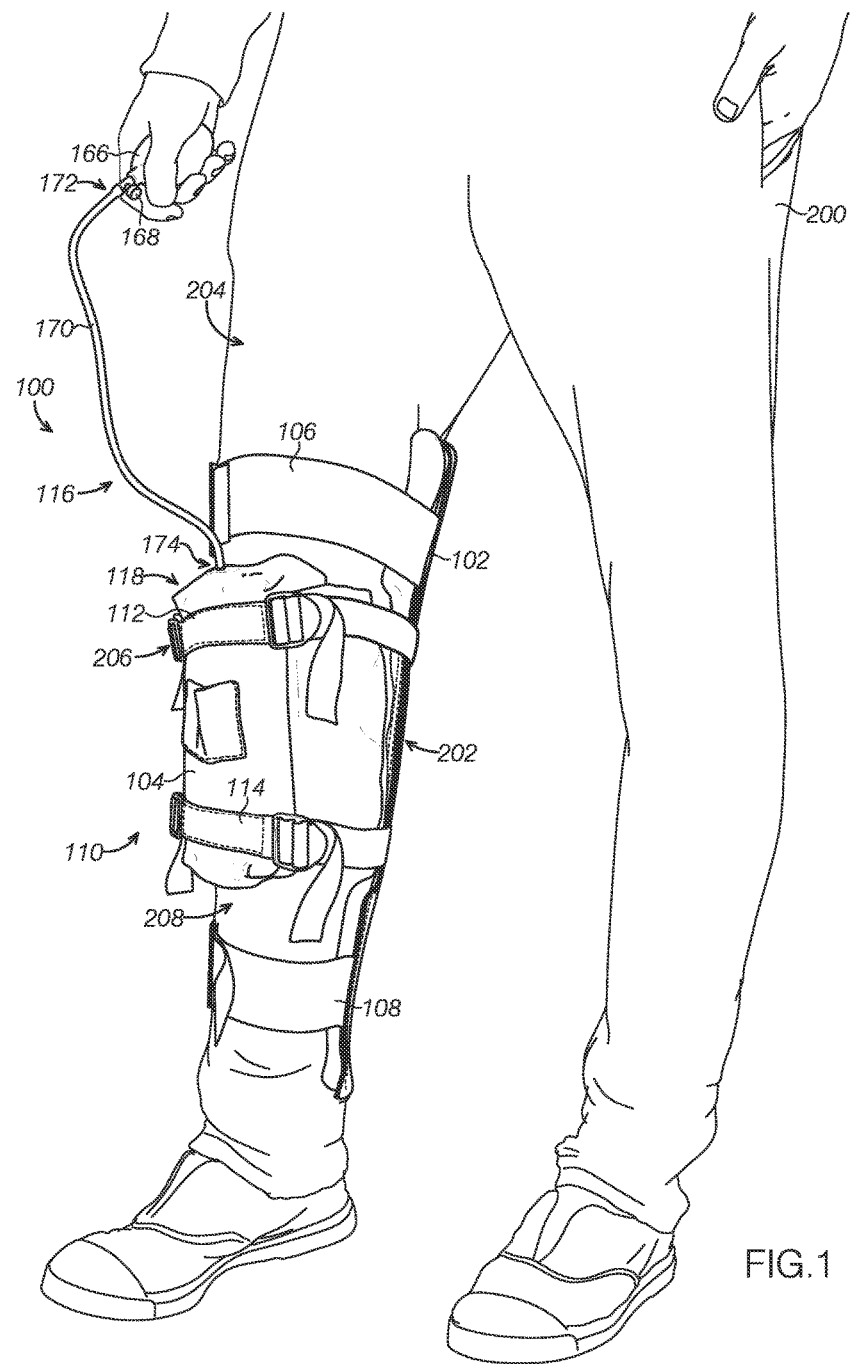
FIG. 1 is a perspective view of a first example of an adjustable leg brace for straightening of a patient's leg, depicting a user wearing the leg brace.

As can be seen in FIG. 1, leg brace 100 is wearable by a user 200 and includes a posterior brace 102 and an anterior brace 104. Posterior brace 102 is a substantially rigid elongate body configured to be braced against and/or abutted to a rear (i.e., posterior) portion 202 of the user's leg 204. Further, posterior brace 102 includes an upper attachment mechanism 106 for attachment of the base to a region of leg 204 above a knee joint 206 and a lower attachment mechanism 108 for attachment of the base to a region of leg 204 below knee joint 206. In the present example, upper attachment mechanism 106 includes a strap that encompasses the user's thigh and the lower attachment mechanism 108 includes a strap that encompasses the user's shin. In other examples, the upper and lower attachment mechanisms can include additional straps and/or other attachment components (e.g., snaps, buckles, hook and loop material, etc.).

In opposition to posterior brace 102, anterior brace 104 is configured to be braced and/or abutted to a front (i.e., anterior) portion 208 of leg 204, proximal to and/or on knee joint 206. Anterior brace 104 includes an attachment mechanism 110 for attaching anterior brace 104 to posterior brace 102. In the present example, attachment mechanism 110 includes an upper strap 112 and a lower strap 114. In other examples, the attachment mechanism for the anterior brace can have more or fewer straps and/or other attachment components (e.g., snaps, buckles, hook and loop material, etc.). In even other examples, the posterior brace can be excluded and the anterior brace can be attached to a standard leg brace and/or some other rigid or semi-rigid structure on the posterior side of the leg.

Figure 11:
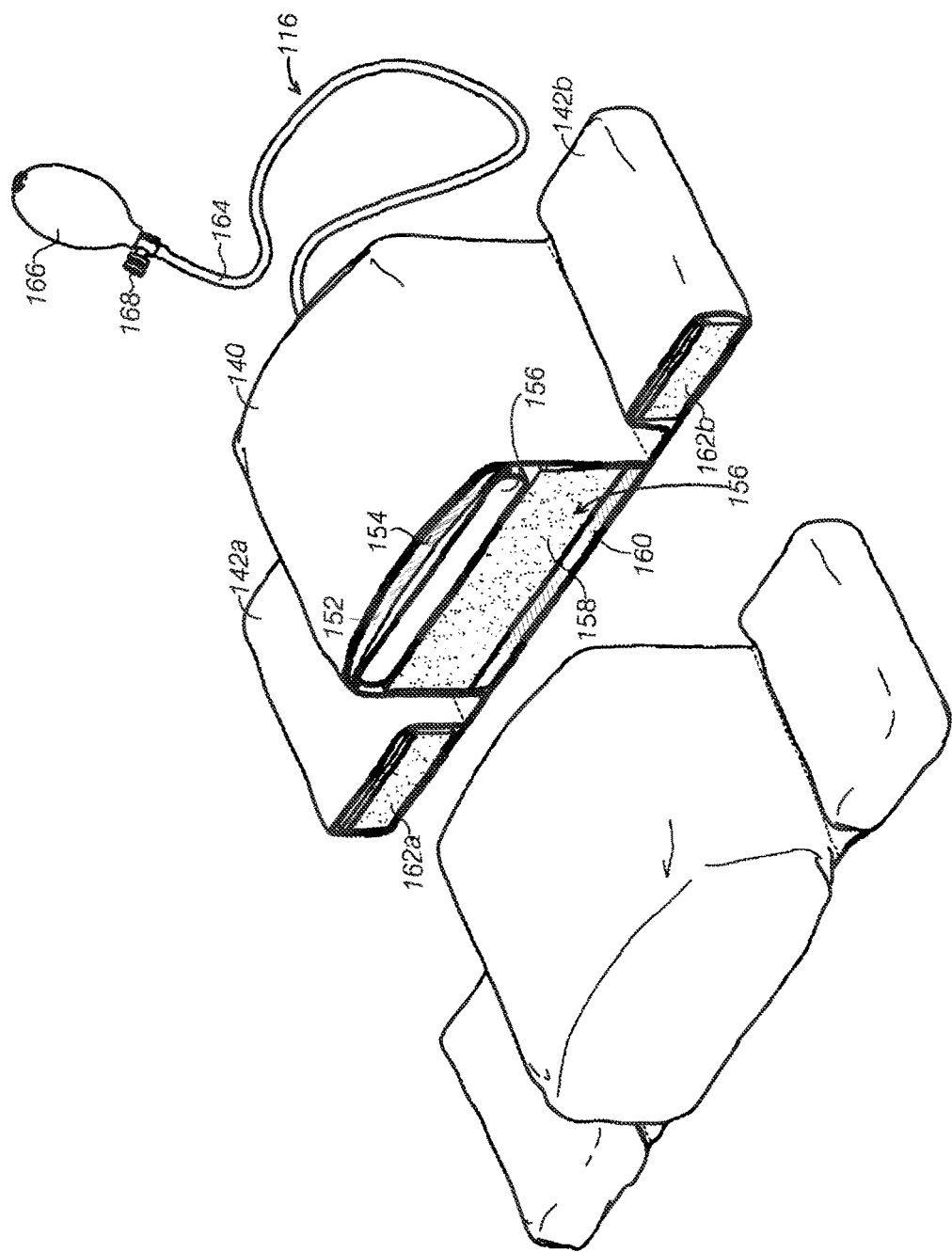
FIG. 11 is a cross-sectional view of the anterior brace of the first example adjustable leg brace shown in FIG. 1.

Anterior brace 104 further includes a bladder 156 (shown in FIG. 11). Bladder 156 is selectively expandable and selectively contractible via actuation of an expansion and contraction regulation mechanism 116. Expansion and contraction regulation mechanism 116 is disposed on an upper end 118 of anterior brace 104 so that is easily manipulated by the user during wear for expansion and contraction of bladder 156. In an expanded state, the bladder puts pressure on the knee and thereby urges the leg towards an extended position. The degree of pressure is regulated by the user via the expansion and contraction regulation mechanism as desired by the user dependent on pain tolerance, effectiveness, strength of the knee, etc.

FIGS. 2-11 show more detailed perspective views of leg brace 100. As shown in FIGS. 2-9, posterior brace 102 includes a rigid base 120. The rigid base is comprised of a rigid or semi-rigid material, such as injection molded polycarbonate plastic. Posterior brace 102 further includes pads 122 and 124. Specifically, pad 122 is disposed an upper portion 126 of posterior brace 102 and is shaped as to receive a posterior side of the user's upper leg (i.e., thigh). Pad 124 is disposed on a lower portion 128 of posterior brace 102 and is shaped as to receive a posterior side of the user's lower leg (i.e., calf). Each of pads 122 and 124 are comprised of a moderately compressible material (e.g., foam, gel, etc.) and are configured to at least partially conform to the shape of the user's leg during wear.

Figure 8:
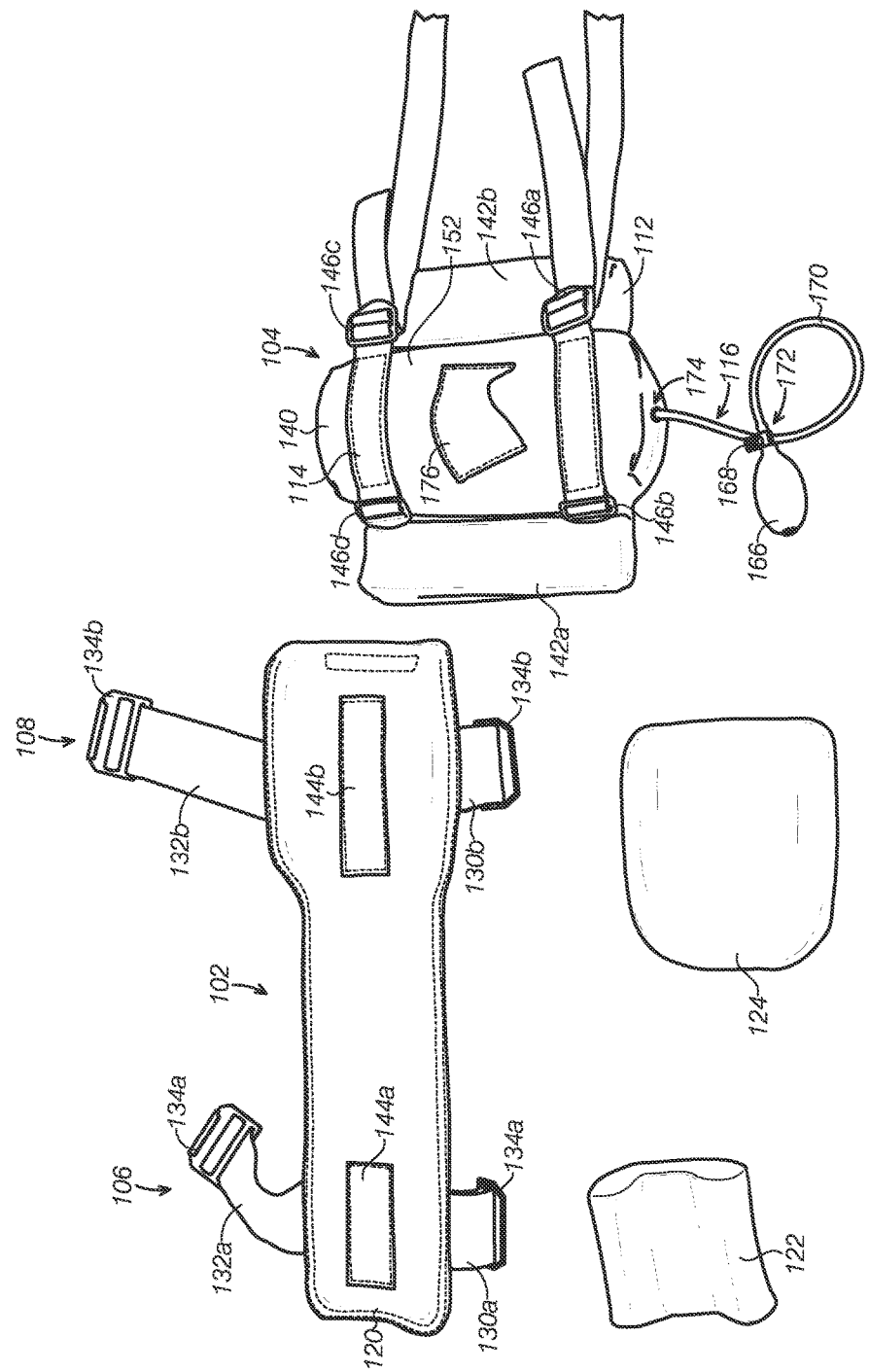
FIG. 8 is a top perspective view of the first example adjustable leg brace shown in FIG. 1, depicting the components of the leg brace is a disassembled form.
Figure 9:
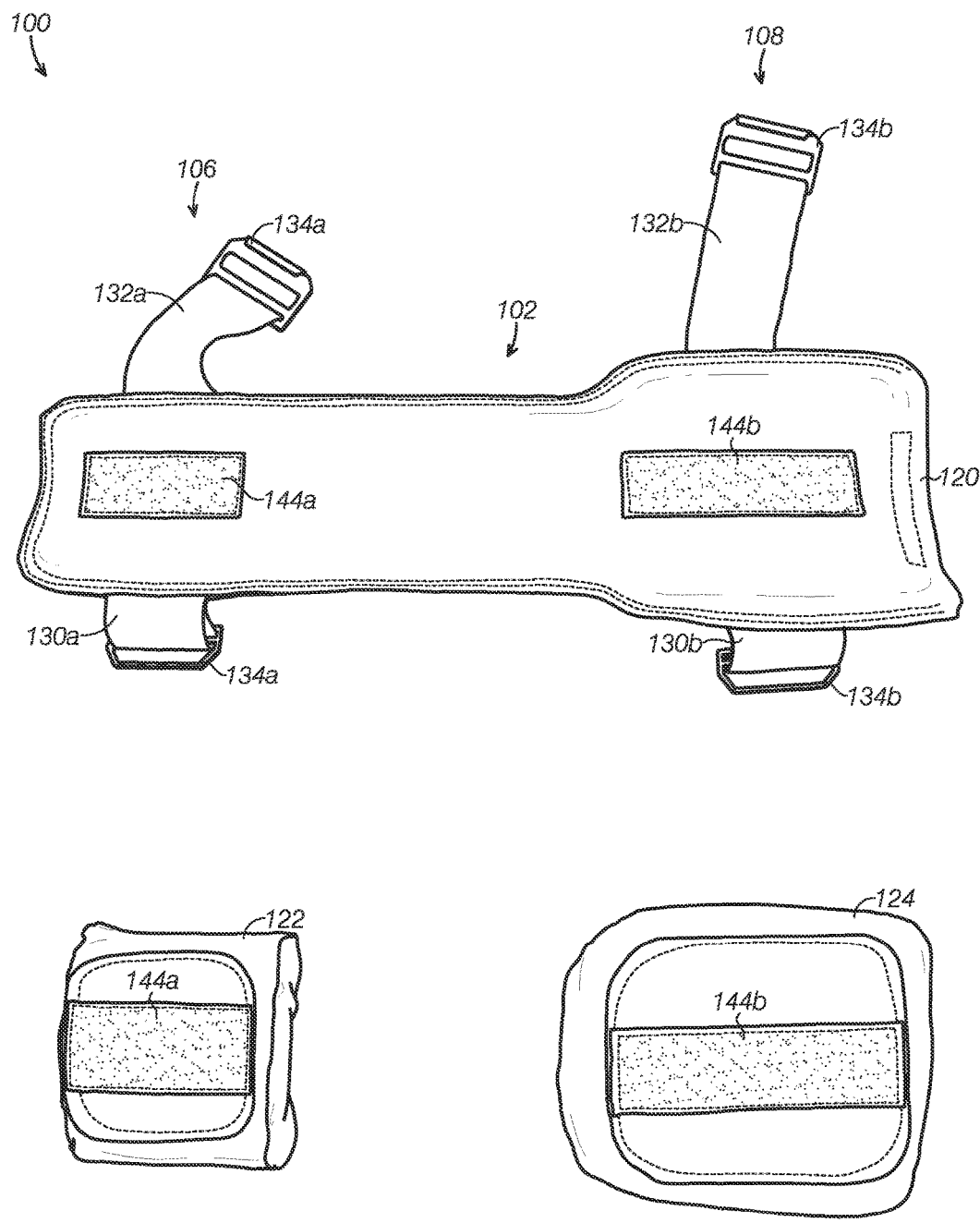
FIG. 9 is a top perspective view of the posterior brace of the first example adjustable leg brace shown in FIG. 1, depicting the components of the posterior brace in a disassembled form.

In some examples, the pads can be permanently fixed to the rigid base (e.g., sewn, adhered, etc.) In the present example, however, the pads are selectively attachable to the rigid base. As depicted in FIGS. 8 and 9, pads 122 and 124 are selectively removable from rigid base 120. Specifically, base 120 and pads 122 and 124 includes pad attachment mechanisms 144a and 144b disposed on an inner surface of the rigid base an on a non-body contacting surface of the pads. In the present example, pad attachment mechanisms 144a and 144b are complimentary hook and loop material (e.g., Velcro®). In other examples, the pad attachment mechanisms can have a different configuration (e.g., snaps, magnets, etc.).

As stated above, posterior brace 102 additionally includes upper attachment mechanism 106 and lower attachment mechanism 108. Each of the upper and lower attachment mechanisms has a first band (130a and 130b) that is matable to a second band (132a and 132b) for encompassing the user's leg at their respective attachment regions. In the present example, each of the bands is comprised of a substantially elastic and sturdy material (e.g., 62% nylon and 38% emulsion silk). In other examples, the bands can be comprised of a non-elastic sturdy material (e.g., canvas, nylon, etc.) and include a tightening mechanism for securing the upper and lower attachment mechanisms to the user's leg.

Figure 2:
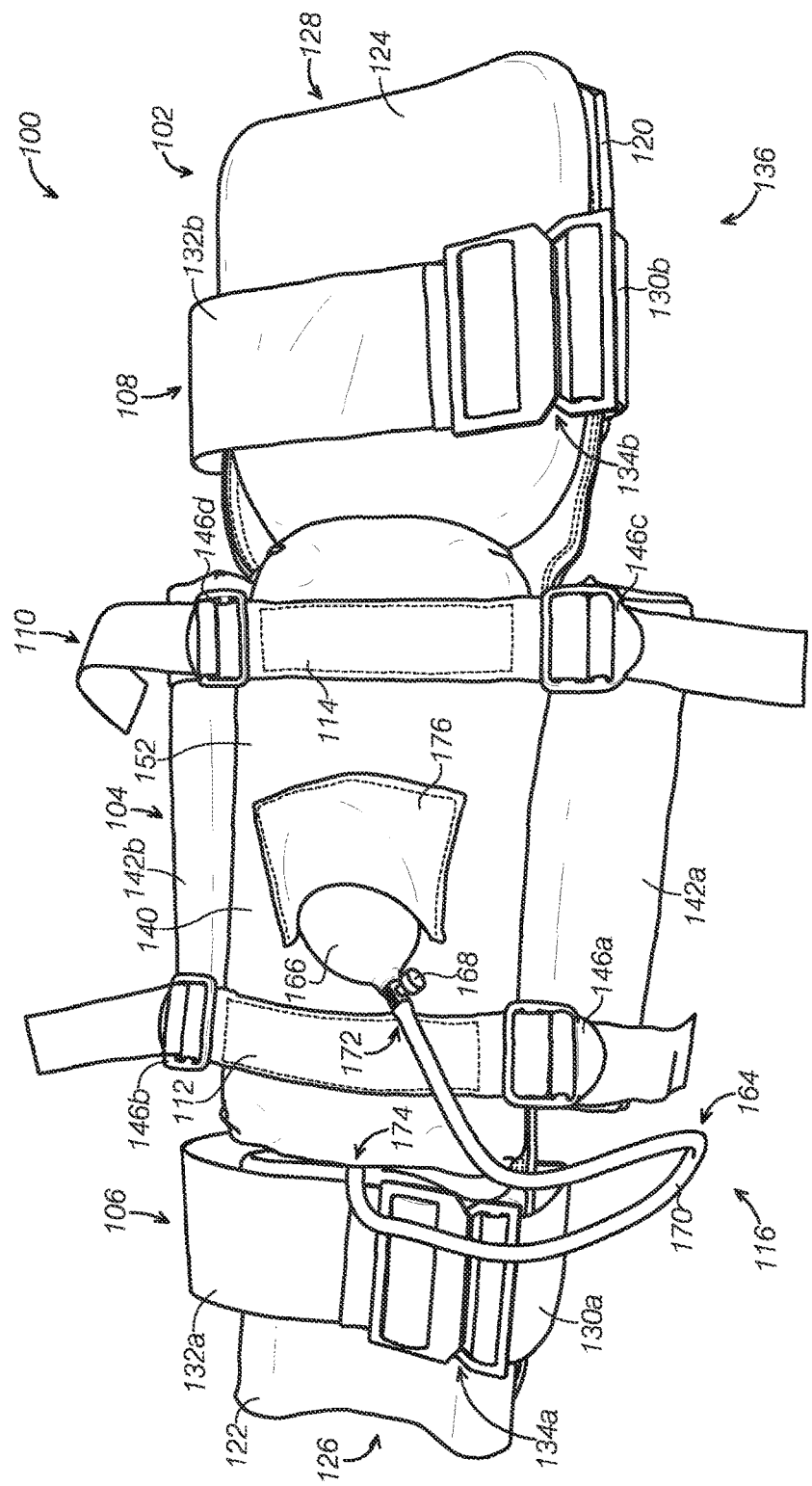
FIG. 2 is a top perspective view of the first example adjustable leg brace shown in FIG. 1, depicting the base attachment mechanisms in a coupled position.
Figure 3:
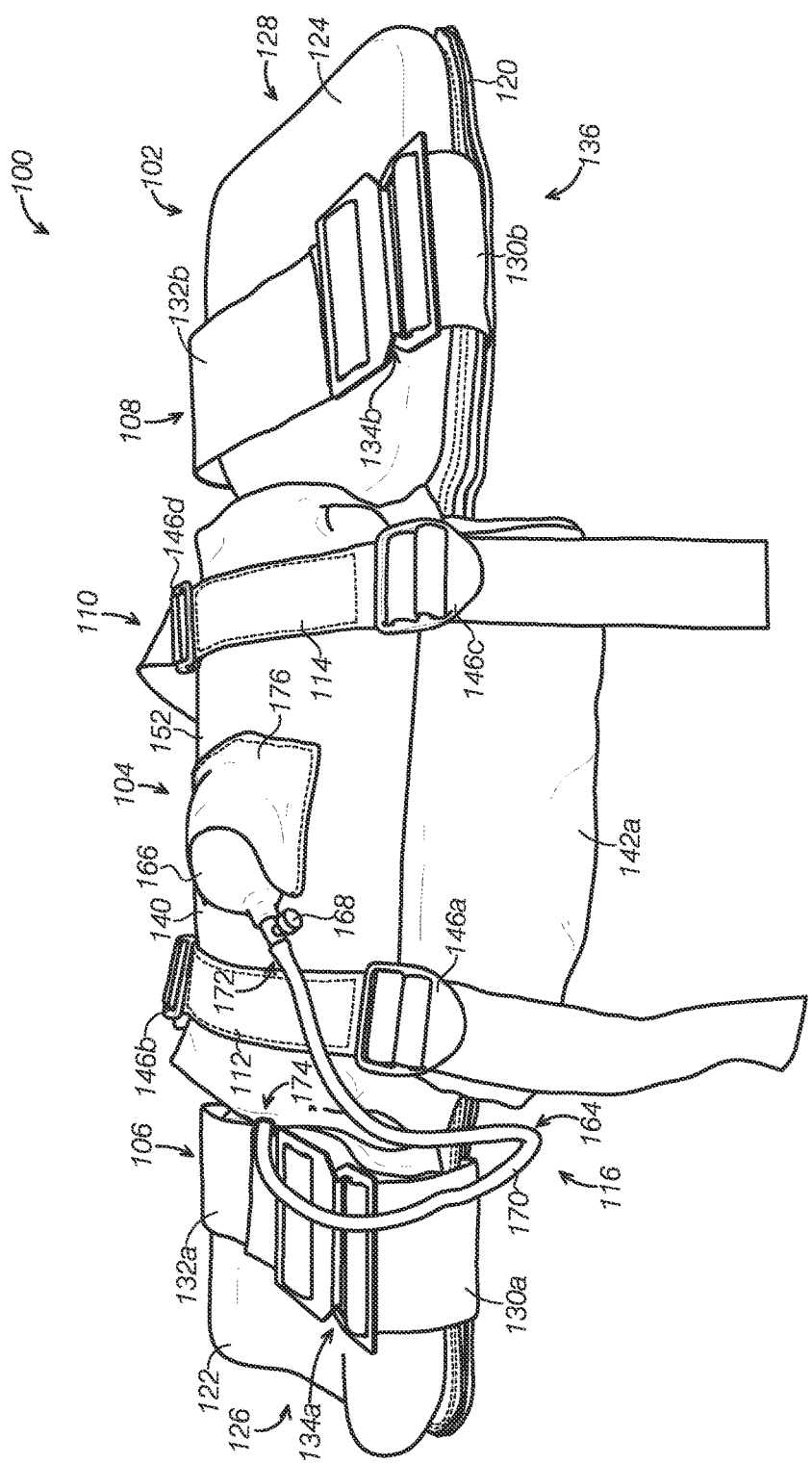
FIG. 3 is a front perspective view of the first example adjustable leg brace shown in FIG. 1.
Figure 4:
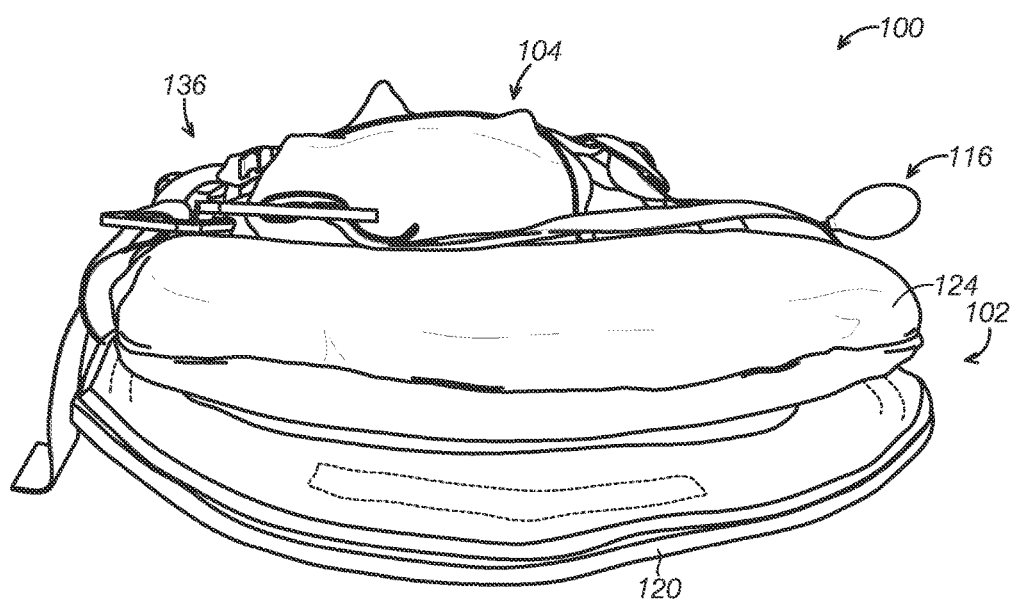
FIG. 4 is a side perspective view of the first example adjustable leg brace shown in FIG. 1.
Figure 5:
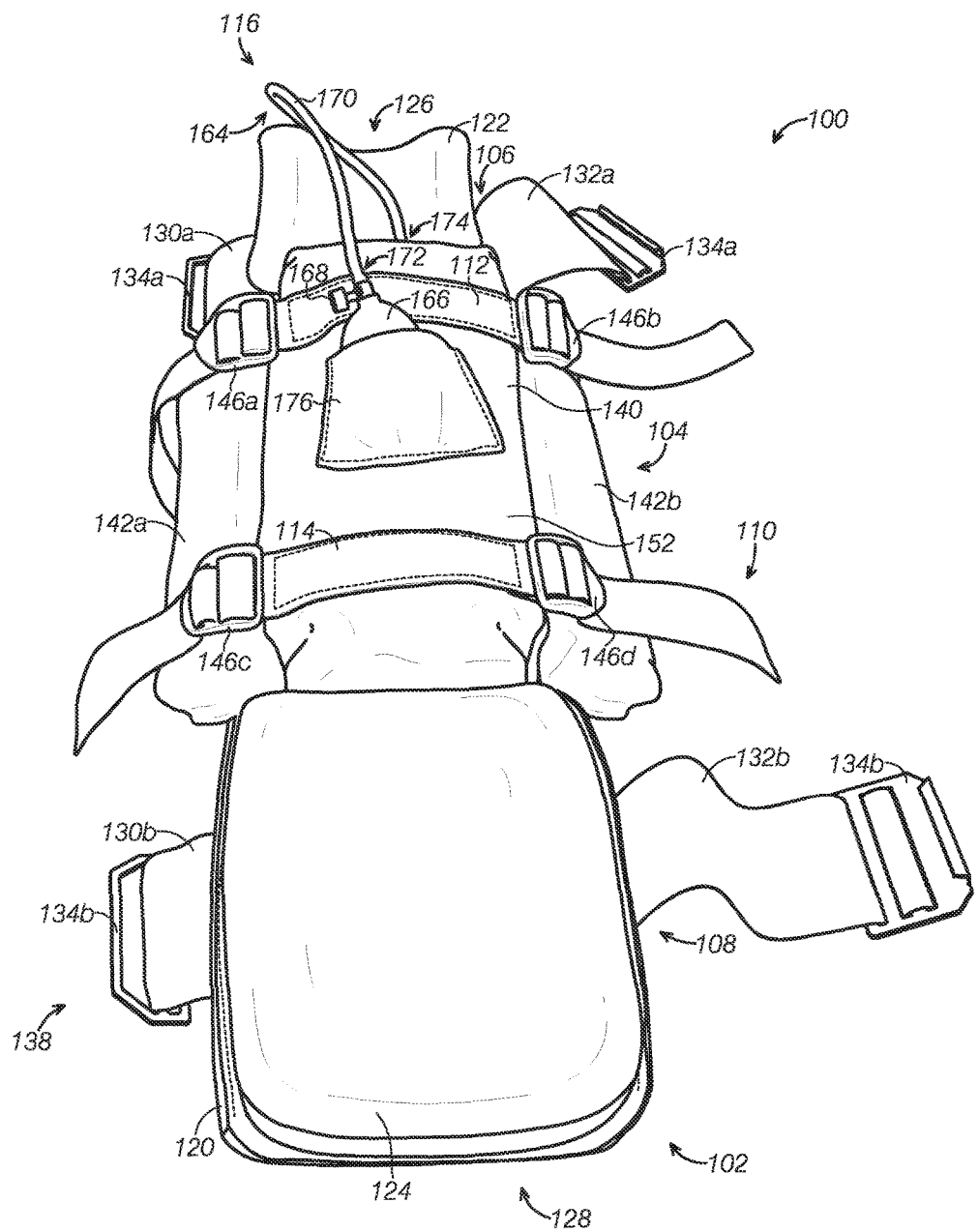
FIG. 5 is a top longitudinal perspective view of the first example adjustable leg brace shown in FIG. 1, depicting the base attachment mechanisms in an un-coupled position.
Figure 6:
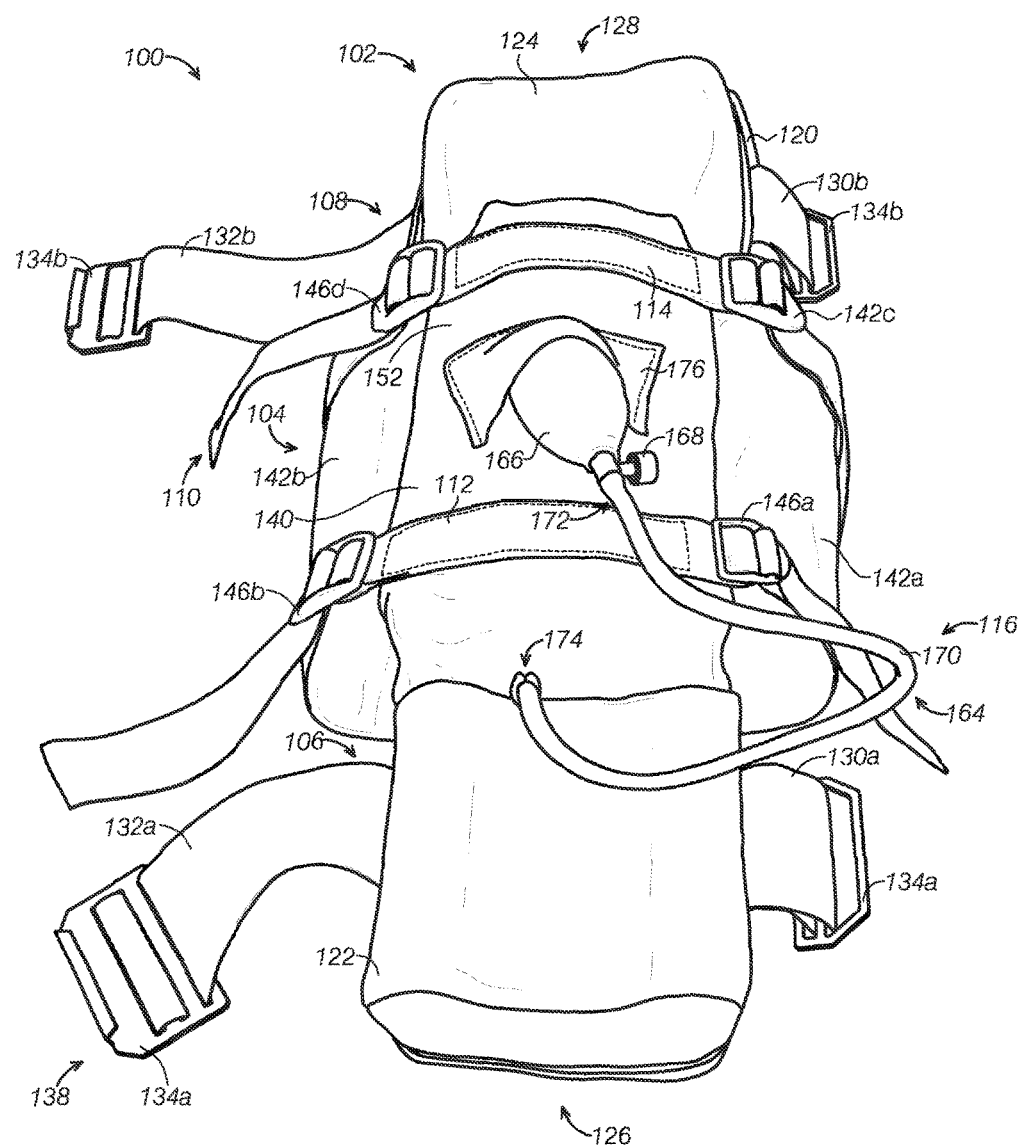
FIG. 6 is a top longitudinal perspective view of the first example adjustable leg brace shown in FIG. 1, depicting the base attachment mechanisms in an un-coupled position.
Figure 7:
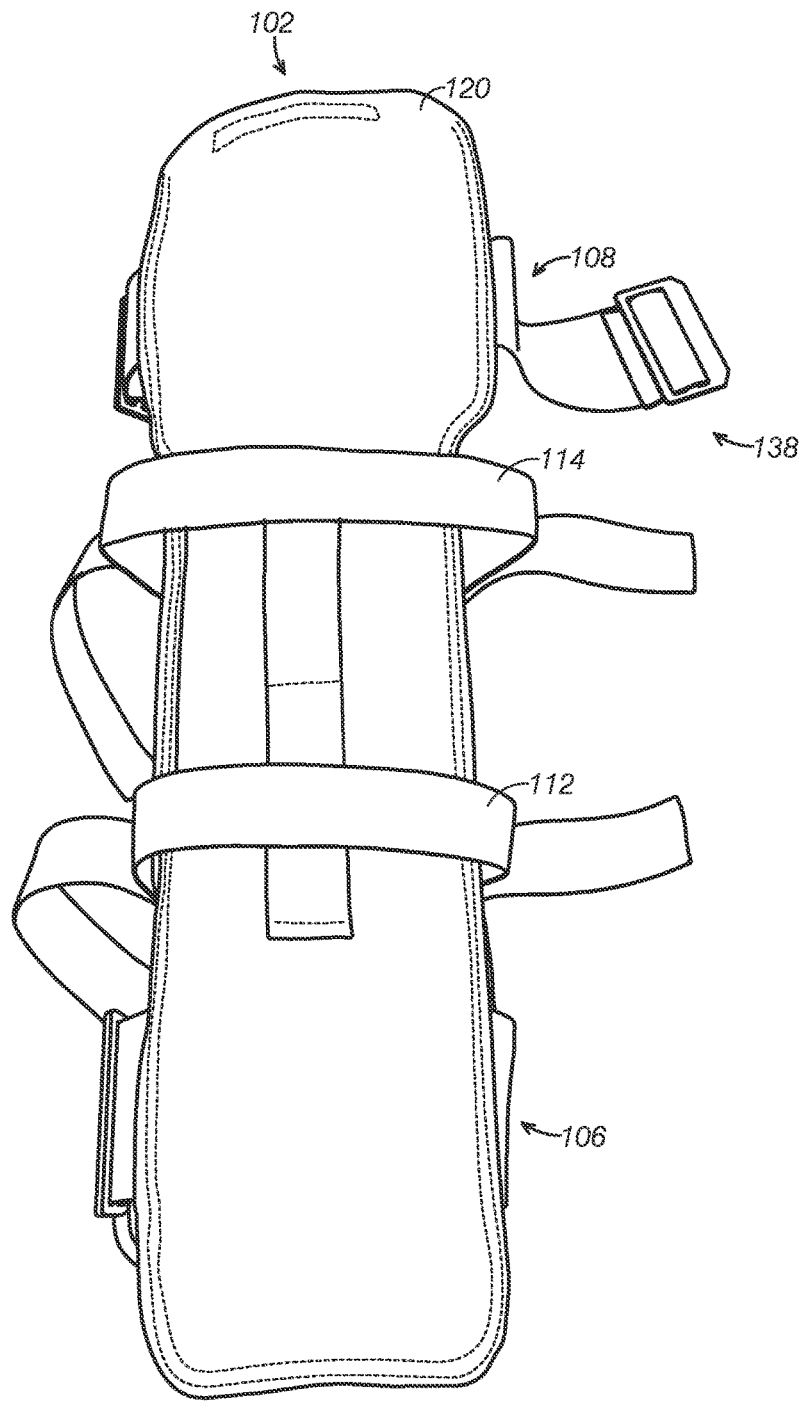
FIG. 7 is a top longitudinal perspective view of the first example adjustable leg brace shown in FIG. 1, depicting the base attachment mechanisms in an un-coupled position.

In the present example, each of upper attachment mechanism 106 and lower attachment mechanism 108 are selectively attachable around the user's leg via a coupling mechanism 134a and 134b, respectively. FIGS. 2-4 show both coupling mechanisms 134a and 134b in a coupled position 136, while FIGS. 5-7 show the coupling mechanisms in an uncoupled position 138. In the present example, each of the coupling mechanisms includes a laterally elongate hook fittable into a complimentarily configured eye for coupling and uncoupling of the posterior brace attachment mechanism.

It will be appreciated that in alternate examples the upper and lower attachment mechanisms can have a different configuration. For example, the upper and lower attachment mechanisms can each include selectively looseanable and tightenable loops, in which the user's legs can be inserted through when loosened and then attached to the posterior leg brace via tightening of the loops. In another example, the coupling mechanism can have a different configuration, such as a snap-fit buckle, hook and loop material, or any another appropriate coupling mechanism known or yet to be discovered.

Returning to FIGS. 2-8, 10, and 11, as described above, anterior brace 104 includes expansion and contraction regulation mechanism 116 and attachment mechanism 110 having upper strap 112 and lower strap 114. Anterior brace 104 further includes a central body 140 and adjacent side bodies 142a and 142b. Side bodies 142a and 142b are substantially cushioning bodies comprised of a moderately compressible material (e.g., foam, gel, etc.) and are configured to at least partially conform to the shape of the user's leg during wear, while central body 140 houses bladder XX. In alternate examples, the anterior base can include more or fewer cushioning side bodies.

Figure 10A:
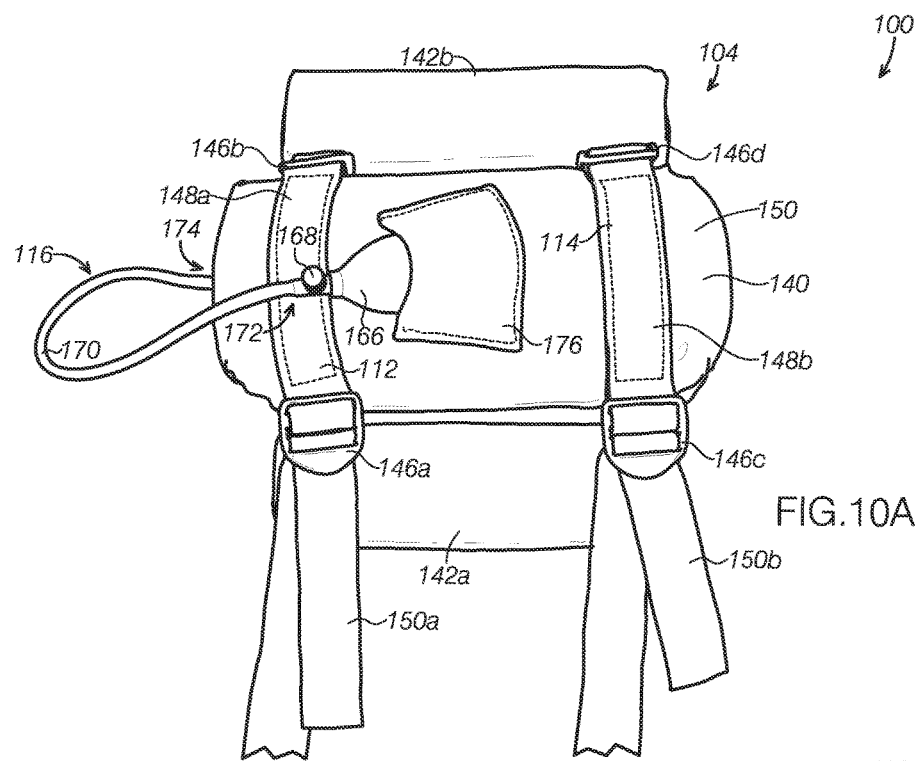
FIGS. 10A and 10B are a top perspective view and a side perspective view, respectively, of the anterior brace of the first example adjustable leg brace shown in FIG. 1.
Figure 10B:
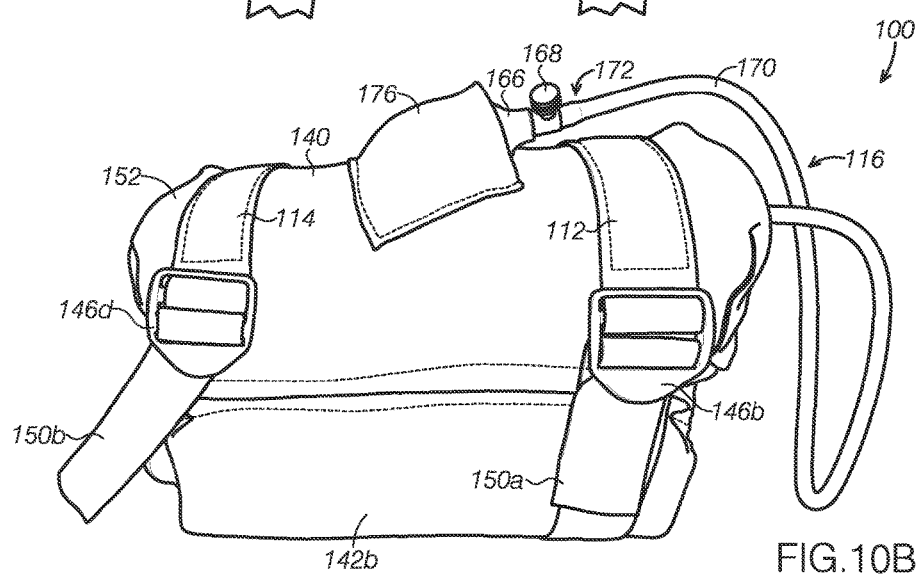

As depicted in FIGS. 8, 10A, and 10B, anterior brace 104 is detachable from posterior brace 102. In other examples, the anterior brace can be fixed to (i.e., non-detachable from) the posterior brace via the anterior brace attachment mechanism. In the present example, anterior brace 104 can be used alone or in combination with posterior brace 102 and/or another posterior bracing mechanism.

Straps 112 and 114 are non-elastic straps configured to extend around the user's leg and/or an outer surface of posterior brace 102 (depicted in FIG. 7). In the present example, straps 112 and 114 are each attachable/releasable and tightenable via tension buckles 146a-146d. Specifically, a fixed portion 148a strap 112 is fixedly attached to an outer surface of anterior brace 104. Tensioning buckles 146a and 146b are fixed to opposing ends of fixed portion 148a. Opposing ends of a loose portion 150a of strap 112 are threadable through tension buckles 146a and 146b for closing and/or tightening of strap 112 around the user's leg and/or the posterior brace. Further, a fixed portion 148b strap 114 is fixedly attached to an outer surface of anterior brace 104. Tensioning buckles 146c and 146d are fixed to opposing ends of fixed portion 148b. Opposing ends of a loose portion 150b of strap 114 are threadable through tension buckles 146c and 146d for closing and/or tightening of strap 114 around the user's leg and/or the posterior brace. The anterior brace attachment mechanism has the advantage that it is tightenable on both sides of the brace so that it can remain positioned over the knee during adjustment of the attachment mechanism.

It will be appreciated that in alternate examples the anterior brace can be attached to the user's leg and/or the posterior brace via a different mechanism. In one example, the anterior brace can include one or more elastic and/or non-elastic bands that are fixed to one side of the anterior brace and can be wrapped around the user's leg and/or the posterior brace. The free end of the one or more bands can include an attachment mechanism (e.g., hook and loop material, snaps, buckles, etc.) for substantially retaining a position of the one or more elastic bands until they are released by the user and/or a tightening mechanism. It will be further appreciated that in other alternate examples, the anterior brace can include any known mechanism for attachment of the anterior brace to the leg of the user and/or the posterior brace or any mechanism yet to be discovered.

A cross-section of central body 140 and side bodies 142a and 142b is shown in FIG. 11. As depicted in FIG. 11, central body 140 and side bodies 142a and 142b are joined by a flexible covering 152, such as a material covering (e.g., neoprene, elastic mesh, spandex, etc.) that encloses the central body and the side bodies. Proximal to the outer surface of the central body, a shell 154 is disposed under covering 152. The rigid shell is comprised of a rigid material, such as injection molded poly carbonate plastic. Shell 154 is configured to support bladder 154, particularly during expansion of the bladder (described in greater detail below).

Bladder 156 is disposed between shell 154 and a pad 156. The pad is comprised of a compressible material configured to at least partially conform to an anterior portion of the user's leg (e.g., the knee) during wear. In the present example, padding layer 156 includes a foam layer 158 (e.g., poly urethane foam, etc.) and a gel layer 160 (e.g., silicone, etc.) and is disposed on an inner surface of bladder 156. In alternate examples, the pad can include more of fewer layers of different or similar materials and/or additional padding layers between the shell and the outer surface of the bladder. Further, side bodies 142a and 142b include pads 162a and 162b, respectively, configured to at least partially conform to the sides of the anterior portion of the user's leg (i.e., sides of the knee). In the present example, pads 162a and 162b are foam pads, however, in alternate examples, the pads can include additional layers of similar and/or different materials (e.g., gel pads, foam layers, etc.).

As described above, bladder 156 is selectively expandable and contractible via actuation of expansion and contraction regulation mechanism 116. Specifically, in the present example, expansion and contraction regulation mechanism 116 is an air pump 164 having a hand actuator bulb 166, a release valve 168, and a flexible tube 170 (shown in FIGS. 1-3, 5, 6, 8, and 10A-11).

A first end 172 of tube 170 is in fluid communication with actuator bulb 166 and forms an air tight seal with the actuator bulb. A second end 174 of tube 170 is in fluid communication with bladder 156 (disposed inside of posterior brace 104) and forms an air tight seal with the bladder. As depicted in FIG. 1, tube 170 has a length that is adequate for a user hold and/or grasp bulb 166 in the user's hand so that the bulb and/or the release valve can be actuated by the user during wear of the leg brace.

Accordingly, the user can actuate the bulb to input air into the bladder and move the bladder into the expanded state. A position of the bladder is substantially maintained (i.e., movement of the bladder is limited) by the attachment of anterior brace attachment mechanism to the posterior brace and the shell. Specifically, the anterior brace attachment mechanism is attached to the shell (e.g., sewn and/or adhered to the flexible covering, etc.) and is configured to limit movement of the shell. By limiting movement of the shell, the shell is compressed against the bladder and the bladder is compressed against the anterior side of the user's leg when the bladder is in the expanded state.

As described above, the bladder puts pressure on the knee and thereby urges the leg towards an extended position when in the expanded state, and the degree of pressure is regulated by the user via the expansion and contraction regulation mechanism as desired by the user dependent on pain tolerance, effectiveness, strength of the knee, etc. To release air from bladder 156 (i.e., to move the bladder into a contracted state), the user can actuate (i.e., open) release valve 168 such that air is released from the bladder. When not in use, bulb 166 can be stored in a pocket 176 on an outer surface of covering 152 (as depicted in FIGS. 2, 3, 5, 6, 10A, and 10B).

In alternate examples, expansion and contraction of the bladder can be regulated by a different mechanism. For example, the expansion and contraction mechanism can be an automated mechanical pump that can be actuated by the user via one more control buttons and/or switches. In this example, the control buttons and/or switches can be located on a cord and/or disposed on a surface of the anterior brace. In even other alternate examples, the bladder can be selectively expandable and contractible via a substance other than air, such as a fluid or a semi-fluid substance (e.g., water, gel, etc.). In these other alternate examples, the expansion and contraction mechanism can be configured to pump the fluid or semi-fluid substance in and out of the bladder via a user actuatable mechanism.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. An apparatus, comprising:
a posterior brace configured to be braced against a posterior portion of a leg, the posterior brace comprising:
an elongate base, the elongate base being a substantially rigid elongate base;
an upper posterior brace attachment mechanism for attaching the posterior brace to a first region of the leg above a knee joint; and
a lower posterior brace attachment mechanism for attaching the posterior brace to a second region of the leg below the knee joint; and
an anterior brace configured to be braced against an anterior portion of the leg at the knee joint, the anterior brace comprising:
a bladder that is selectively expandable and selectively contractible, the bladder having an inner surface that is configured to be proximal to the knee joint of the leg, wherein:
the bladder is operable to put pressure on the knee joint to urge the leg towards an extended position; and
the inner surface of the bladder is configured to cover the entire knee joint such that when the bladder is filled the bladder urges the entire knee joint into a straight position, and
an anterior brace attachment mechanism for attaching the anterior brace to the posterior brace.

2. The apparatus of claim 1, further comprising an expansion and contraction regulation mechanism for selectively expanding and selectively contracting the bladder.

3. The apparatus of claim 2, wherein the bladder is selectively fillable with air and the expansion and contraction regulation mechanism is an air pump, the air pump being fluidly connected to the bladder.

4. The apparatus of claim 3, wherein the air pump comprises a hand pump for selectively expanding the bladder and a release valve for selectively contracting the bladder.

5. The apparatus of claim 3, wherein the air pump is disposed on a top portion of the anterior brace when a user is in an upright position.

6. The apparatus of claim 1, wherein the anterior brace further comprises a shell configured to support the bladder, the shell being comprised of a rigid material and being disposed proximal to an outer surface of the bladder, the outer surface of the bladder opposing the inner surface of the bladder.

7. The apparatus of claim 6, wherein the anterior brace attachment mechanism is attached to the shell, the anterior brace attachment mechanism being configured to limit movement of the shell when the bladder is in an expanded state, and thereby compress the shell against the bladder and compress the bladder against the anterior portion of the leg.

8. The apparatus of claim 1, wherein the anterior brace attachment mechanism comprises one or more straps that are selectively attachable and tightenable around the region of the leg proximal to the knee and an outer surface of the posterior brace.

9. The apparatus of claim 8, wherein the one or more straps comprise an upper strap and a lower strap, the upper strap configured to attach a top portion of the anterior brace to the posterior brace and the lower strap configured to attach a lower portion of the anterior brace to the posterior brace.

10. The apparatus of claim 1, wherein the upper posterior brace attachment mechanism comprises a strap that is selectively attachable and tightenable around the region of the leg above the knee joint.

11. The apparatus of claim 1, wherein the lower posterior brace attachment mechanism comprises a strap that is selectively attachable and tightenable around the region of the leg below the knee joint.

12. The apparatus of claim 1, further comprising a posterior brace padding attached to an inner surface of the posterior brace, the posterior brace padding being a compressible material configured to at least partially conform to a shape of the posterior portion of the leg during wear of the apparatus.

13. The apparatus of claim 1, further comprising an anterior brace padding attached to the inner surface of the bladder, the anterior brace padding being a compressible material configured to at least partially conform to a shape of the anterior portion of the leg during wear of the apparatus.

14. An apparatus, comprising:
an anterior brace configured to be braced against an anterior portion of a leg at a knee joint and attachable to a posterior brace braced against a posterior portion of the leg, the anterior brace comprising:
a bladder that is selectively expandable and selectively contractible, the bladder comprising an inner surface that is configured to be proximal to the knee joint of the leg, wherein the bladder is operable to put pressure on the knee joint to urge the leg towards an extended position;
an expansion and contraction regulation mechanism for selectively expanding and contracting the bladder;
a shell configured to support the bladder, the shell being comprised of a rigid material and being disposed proximal to an outer surface of the bladder, the outer surface of the bladder opposing the inner surface of the bladder; and
an anterior brace attachment mechanism for attaching the anterior brace to the posterior brace, the anterior brace attachment mechanism being attached to the shell, the anterior brace attachment mechanism being configured to limit movement of the shell when the bladder is in an expanded state, and thereby compress the shell against the bladder and compress the bladder against the anterior portion of the leg, wherein the inner surface of the bladder is configured to cover the entire knee such that when the bladder is filled the bladder urges the entire knee into a straight position.

15. The apparatus of claim 14, wherein the bladder is selectively fillable with air and the expansion and contraction regulation mechanism is an air pump, the air pump being fluidly connected to the bladder.

16. The apparatus of claim 15, wherein the air pump is disposed on a top portion of the anterior brace when a user is in an upright position.

17. The apparatus of claim 14, further comprising the posterior brace the posterior brace being configured to be braced against a posterior portion of the leg, the posterior brace comprising:
- an elongate base, the elongate base being a substantially rigid elongate base,
- an upper posterior brace attachment mechanism for attaching the posterior brace to a first region of the leg above the knee joint, and
- a lower posterior brace attachment mechanism for attaching the posterior brace to a second region of the leg below the knee joint.

18. The apparatus of claim 14, wherein the anterior brace attachment mechanism comprises one or more non-elastic straps that are selectively attachable and tightenable around an outer surface of the posterior brace.

19. The apparatus of claim 14, further comprising an anterior brace padding attached to the inner surface of the anterior brace, the anterior brace padding being a compressible material configured to at least partially conform to a shape of the anterior portion of the leg during wear of the anterior brace.

20. A device comprising:
- a posterior brace configured to be braced against a posterior portion of a leg, the posterior brace comprising:
  - an elongate base, the elongate base being a substantially rigid elongate base;
  - an upper posterior brace attachment mechanism for attaching the posterior brace to a first region of the leg above a knee joint; and
  - a lower posterior brace attachment mechanism for attaching the posterior brace to a second region of the leg below the knee joint; and
- an anterior brace configured to be braced against an anterior portion of the leg at the knee joint and attachable to the posterior brace, the anterior brace comprising:
  - a bladder that is selectively expandable and selectively contractible, the bladder comprising an inner surface that is configured to be proximal to the knee joint of the leg, wherein:
    - the bladder is operable to put pressure on the knee joint to urge the leg towards an extended position; and
    - the inner surface of the bladder is configured to cover the entire knee such that when the bladder is filled the bladder urges the entire knee into a straight position;
  - an anterior brace attachment mechanism for attaching the anterior brace to the posterior brace;
  - an expansion and contraction regulation mechanism for selectively expanding and contracting the bladder; and
  - a shell configured to support the bladder, the shell being comprised of a rigid material and being disposed proximal to an outer surface of the bladder, the outer surface of the bladder opposing the inner surface of the bladder.

* * * * *